United States Patent
Martí Seves et al.

(10) Patent No.: US 11,337,980 B2
(45) Date of Patent: May 24, 2022

(54) TREATMENT OF MITOCHONDRIAL DISEASES

(71) Applicants: FUNDACIÓ HOSPITAL UNIVERSITARI VALL D'HEBRON—INSTITUT DE RECERCA, Barcelona (ES); CENTRO DE INVESTIGACIÓN BIOMÉDICA EN RED, Madrid (ES)

(72) Inventors: Ramon Martí Seves, Barcelona (ES); Emiliano González Vioque, Madrid (ES); Cora Blázquez Bermejo, Errenteria (ES); Javier Torres Torronteras, El Prat de Llobregat (ES); Raquel Cabrera Pérez, Sant Boi de Llobregat (ES); Yolanda Cámara Navarro, Barcelona (ES)

(73) Assignees: FUNDACIÓ HOSPITAL UNIVERSITARI VALL D'HEBRON-INSTITUT DE RECERCA, Barcelona (ES); CENTRO DE INVESTIGACIÓN BIOMÉDICA EN RED, Madrid (ES)

( * ) Notice: Subject to any disclaimer, the term of this patent is extended or adjusted under 35 U.S.C. 154(b) by 0 days.

(21) Appl. No.: 15/578,621

(22) PCT Filed: Jun. 3, 2016

(86) PCT No.: PCT/EP2016/062636
§ 371 (c)(1),
(2) Date: Nov. 30, 2017

(87) PCT Pub. No.: WO2016/193421
PCT Pub. Date: Dec. 8, 2016

(65) Prior Publication Data
US 2018/0161332 A1 Jun. 14, 2018

(30) Foreign Application Priority Data

Jun. 5, 2015 (EP) .................................. 15170825

(51) Int. Cl.
*A61K 31/52* (2006.01)
*A61K 45/06* (2006.01)
*A61K 31/7068* (2006.01)
*A61K 31/7076* (2006.01)
*A61K 31/708* (2006.01)
*A61K 31/7072* (2006.01)
*A61P 3/00* (2006.01)

(52) U.S. Cl.
CPC ............ *A61K 31/52* (2013.01); *A61K 31/708* (2013.01); *A61K 31/7068* (2013.01); *A61K 31/7072* (2013.01); *A61K 31/7076* (2013.01); *A61K 45/06* (2013.01); *A61P 3/00* (2018.01); *A61K 2300/00* (2013.01)

(58) Field of Classification Search
CPC . A61K 31/52; A61K 31/7068; A61K 31/7072
See application file for complete search history.

(56) References Cited

U.S. PATENT DOCUMENTS 5,246,708 A 9/1993 Von Borstel

FOREIGN PATENT DOCUMENTS

| CN | 104524546 A | 4/2015 |
|---|---|---|
| EP | 0509470 | 10/1992 |
| WO | WO 00/50043 A1 | 8/2000 |

OTHER PUBLICATIONS

Camara (Drug Discovery today; vol. 18, Nos. 19/20, 2013, 950-957).*
Bulst (Human Molecular Genetics; 2009, vol. 18 (9); 1590-1599).*
International Search Report and Written Opinion dated Sep. 6, 2016 for PCT/EP2016/062636, 17 pages.
Amati-Bonneau, Patrizia, et al: "OPA1 mutations induce mitochondrial DNA instability and optic atrophy 'plus' phenotypes", Dec. 24, 2007, Brain 2008, vol. 131, pp. 338-351.
Amiot, Aurelien, et al: "Frequency of Mitochondrial Defects in Patients With Chronic Intestinal Pseudo-Obstruction", Apr. 1, 2009, Gastroenterology 2009, vol. 137, Issue 1, pp. 101-109.
Blakely, Emma L., et al: "MPV17 mutation causes neuropathy and leukoencephalopathy with multiple mtDNA deletions in muscle", Neuromuscular Disorderders Jul. 2012, vol. 22(7) pp. 587-591.
Bonnen, Penelope E., et al: "Mutations in FBXL4 Cause Mitochondrial Encephalopathy and a Disorder of Mitochondrial DNA Maintenance", Ther American Journal of Human Genetics, Sep. 5, 2013, vol. 93, pp. 471-481.
Bourdon, Alilce, et al: "Mutation of RRM2B, encoding p53-controlled ribonucleotide reductase (p53R2), causes severe mitochondrial DNA depletion", May 7, 2007, Nature Genetics, vol. 39, pp. 776-780.

(Continued)

*Primary Examiner* — Pancham Bakshi
(74) *Attorney, Agent, or Firm* — Sterne, Kessler, Goldstein & Fox P.L.L.C.

(57) ABSTRACT

The present invention provides a composition comprising one or more deoxyribonucleosides for use in the treatment of a mitochondrial DNA depletion and/or multiple deletions syndrome provided that the syndrome is not caused by a defect in the deoxyribonucleoside triphosphate (dNTP) metabolism. With the use of the invention there is a recovery in mitochondrial DNA levels independently from the severity of the patient's disease, which confers a great therapeutic value to the invention.

17 Claims, 3 Drawing Sheets
Specification includes a Sequence Listing.

(56) References Cited

OTHER PUBLICATIONS

Bulst, Stefanie, et al: "In vitro supplementation with dAMP/dGMP leads to partial restoration of mtDNA levels in mitochondrial depletion syndromes", Human Molecular Genetics, May 1, 2009, vol. 18, No. 9, pp. 1590-1599.
Cámara, Yolanda, et al: "Administration of deoxyribonucleosides oe inhibition of their catabolism as a pharmacological approach for mitochondrial DNA depletion syndrome", Human Molecular Genetics 2014, May 1, 2014, vol. 23, No. 9, pp. 2459-2467.
Cámara, Yolanda, et al: "Feeding the deoxyribonucleoside salvage pathway to rescue mitochondrial DNA", Oct. 2013, Drug Discovery Today, vol. 18, Nos. 19/20, pp. 950-957.
Copeland, William C. "Defects in mitochondrial DNA replication and human disease", Critical Reviews in Biochemistry and Molecular Biology 2012, vol. 47, No. 1, pp. 64-74.
Copeland, William C. "Defects of Mitochondrial DNA Replication", Journal of Child Neurology Sep. 1, 2014, vol. 29(9), pp. 1216-1224.
Copeland, William C. "Inherited Mitochondrial Diseases of DNA Replication*", Sep. 24, 2007, Annual Review of Medicine 2008, vol. 59, pp. 131-146.
El-Hattab, Ayman W., et al: "Mitochondrial DNA Depletion Syndromes: Review and Updates of Genetic Basis, Manifestations, and Therapeutic Options", Feb. 6, 2013, Neurotherapeutics, vol. 10, No. 2, pp. 186-198.
Gai, Xiaowu, et al: "Mutations in FBXL4, Encoding a Mitochondrial Protein, Cause Early-Onset Mitochondrial Encephalomyopathy", Sep. 5, 2013, The American Journal of Human Genetics, vol. 93, pp. 482-495.
Garone, Caterina, et al: "Deoxypyrimidine monophosphate bypass therapy for thymidine kinase 2 deficiency", Jun. 26, 2014, EMBO Molecular Medicine, vol. 6, No. 8, pp. 1016-1027.
Hakonen, Anna H., et al: "Recessive Twinkle mutations in early onset encephalopathy with mtDNA depletion", Brain, Oct. 5, 2007, Issue 30, pp. 3032-3040.
Korhonen, Jenny A., et al: "Reconstitution of a minimal mtDNA replisome in vitro", The EMBO Journal 2004, Jun. 16, 2004, vol. 23(12), pp. 2423-2429.
Kornblum, Cornelia, et al: "Loss-of-function mutations in MGME1 impair mtDNA replication and cause multisystemic mitochondrial disease", Jan. 13, 2013, Nature Genetics, pp. 1-8.
Krishnan, Shuba, et al: "Transgene Expression of *Drosophila melanogaster* Nucleoside Kinase Reverses Mitochondrial Thymidine Kinase 2 Deficiency", The Journal of Biological Chemistry, Feb. 15, 2013, vol. 288, No. 7, pp. 5072-5079.
Longley, Matthre J., et al: "Mutant POLG2 Disrupts DNA Polymerase γ Subunits and Causes Progressive External Ophthalmoplegia", May 4, 2006, The American Journal of Human Genetics Jun. 2006, vol. 78, pp. 1026-1034.
Mandel, Hanna, et al: "The deoxyguanosine kinase gene is mutated in individuals with depleted hepatocerebral mitochondrial DNA", Nov. 2001, Nature Genetics, vol. 29, pp. 337-341.

Naviaux, Robert K., et al: "Mitochondrial DNA polymerase γ deficiency and mtDNA depletion in a child with Alpers' syndrome", Annals of Neurology Jan. 1999, vol. 45, No. 1, pp. 54-58.
Nishigaki Yutaka, et al: "ND5 is a hot-spot for multiple atypical mitochondrial DNA deletions in mitochondrial neurogastrointestinal encephalomyopathy", Nov. 12, 2003, Human Molecular Genetics 2004, vol. 13, No. 1, pp. 91-101.
Nishino, Ichizo, et al: "Thymidine Phosphorylase Gene Mutations in MNGIE, a Human Mitochondrial Disorder", Jan. 29, 1999, Science, New Series, vol. 283, No. 5402 pp. 689-692.
Nogueira, Celia, et al: "Syndromes associated with mitochondrial DNA depletion", Apr. 3, 2014, Italian Journal of Pediatrics 2014, vol. 40, No. 34, pp. 1-10.
Ostergaard, Elsebet, et al: "A novel missense mutation in SUCLG1 associated with mitochondrial DNA depletion, encephalomyopathic form, with methylmalonic aciduria", Jun. 14, 2009, Eur Journal of Pediatrics 2010, vol. 169, pp. 201-205.
Pontarin, Giovanna, et al: "Mammalian ribonucleotide reductase subunit p53R2 is required for mitochondrial DNA replication and DNA repair in quiescent cells", Aug. 14, 2012, PNAS, vol. 109, No. 33, pp. 13302-13307.
Renaldo, Florence, et al: "MFN2, a new gene responsible for mitochondrial DNA depletion", May 3, 2012, Brain 2012, vol. 135, e223, pp. 1-4.
Ronchi, Dario, et al: "Mutations in DNA2 link progressive myopathy to mitochondrial DNA instability", Feb. 7, 2013, Ther American Journal of Human Genetics, vol. 92, pp. 293-300.
Rouzier, Cecile, et al: "The MFN2 gene is responsible for mitochondrial DNA instability and optic atrophy 'plus' phenotype", Dec. 20, 2011, Brain 2012, vol. 135, pp. 23-34.
Saada, Ann, et al: "Mutant mitochondrial thymidine kinase in mitochondrial DNA depletion myopathy", Oct. 22, 2001, Nature Genetics Nov. 2001, vol. 29, pp. 342-344.
Saito, Keiko, et al: "Pyruvate therapy for mitochondrial DNA depletion syndrome", Biochimica et Biophysica Acta—General Subjects, May 1, 2012, vol. 1820, No. 5, pp. 632-636.
Saneto, Russell P. et al: "Alpers-Huttenlocher Syndrome", Pediatric Neurology Mar. 1, 2013, vol. 48, No. 3, pp. 167-178.
Spinazzola, Antonella, et al: "MPV17 encodes an inner mitochondrial membrane protein and is mutated in infantile hepatic mitochondrial DNA depletion", Apr. 2, 2006, Nature Genetics May 2006, vol. 38, No. 5, pp. 570-575.
Spinazzola, Antonella, et al: "Disorders of nuclear-mitochondrial intergenomic signaling", May 25, 2005, Gene 2005, vol. 354, pp. 162-168.
Suomalainen, Anu, et al: "Mitochondrial DNA depletion syndromes—many genes, common mechanisms", Neuromuscular Disordorders 2010, vol. 20, pp. 429-437.
Walker, U.A., et al: "Uridine in the prevention and treatment of NRTI-related mitochondrial toxicity", Antivir Ther. 2005, PubMed URL: http://www.ncbi.nlm.nih.gov/pubmed/16152713, Jan. 13, 2015, XP002751217.
Wedding, Iselin Marie, et al: "Spastic Paraplegia Type 7 is Associated with Multiple Mitochondrial DNA Deletions", Jan. 2014, PLOS ONE, vol. 9, Issue 1, pp. e86340, pp. 1-8.

* cited by examiner

FIG. 1

>gi|187171277|ref|NP_001119603.1| DNA polymerase subunit gamma-1 [Homo sapiens]

MSRLLWRKVAGATVGPGPVPAPGRWVSSSVPASDPSDGQRRRQQQQQQQQQQQQQPQQPQVLSSEGGQLR
HNPLDIQMLSRGLHEQIFGQGGEMPGEAAVRRSVEHLQKHGLWGQPAVPLPDVELRLPPLYGDNLDQHFR
LLAQKQSLPYLEAANLLLQAQLPPKPPAWAWAEGWTRYGPEGEAVPVAIPEERALVFDVEVCLAEGTCPT
LAVAISPSAWYSWCSQRLVEERYSWTSQLSPADLIPLEVPTGASSPTQRDWQEQLVVGHNVSFDRAHIRE
QYLIQGSRMRFLDTMSMHMAISGLSSFQRSLWIAAKQGKHKVQPPTKQGQKSQRKARRGPAISSWDWLDI
SSVNSLAEVHRLYVGGPPLEKEPRELFVKGTMKDIRENFQDLMQYCAQDVWATHEVFQQQLPLFLERCPH
PVTLAGMLEMGVSYLPVNQNWERYLAEAQGTYEELQREMKKSLMDLANDACQLLSGERYKEDPWLWDLEW
DLQEFKQKKAKKVKKEPATASKLPIEGAGAPGDPMDQEDLGPCSEEEEFQQDVMARACLQKLKGTTELLP
KRPQHLPGHPGWYRKLCPRLDDPAWTPGPSLLSLQMRVTPKLMALTWDGFPLHYSERHGWGYLVPGRRDN
LAKLPTGTTLESAGVVCPYRAIESLYRKHCLEQGKQQLMPQEAGLAEEFLLTDNSAIWQTVEELDYLEVE
AEAKMENLRAAVPGQPLALTARGGPKDTQPSYHHGNGPYNDVDIPGCWFFKLPHKDGNSCNVGSPFAKDF
LPKMEDGTLQAGPGGASGPRALEINKMISFWRNAHKRISSQMVVWLPRSALPRAVIRHPDYDEEGLYGAI
LPQVVTAGTITRRAVEPTWLTASNARPDRVGSELKAMVQAPPGYTLVGADVDSQELWIAAVLGDAHFAGM
HGCTAFGWMTLQGRKSRGTDLHSKTATTVGISREHAKIFNYGRIYGAGQPFAERLLMQFNHRLTQQEAAE
KAQQMYAATKGLRWYRLSDEGEWLVRELNLPVDRTEGGWISLQDLRKVQRETARKSQWKKWEVVAERAWK
GGTESEMFNKLESIATSDIPRTPVLGCCISRALEPSAVQEEFMTSRVNWVVQSSAVDYLHLMLVAMKWLF
EEFAIDGRFCISIHDEVRYLVREEDRYRAALALQITNLLTRCMFAYKLGLNDLPQSVAFFSAVDIDRCLR
KEVTMDCKTPSNPTGMERRYGIPQGEALDIYQIIELTKGSLEKRSQPGP ved with mtDNA replication or maintenance. These rare
TREATMENT OF MITOCHONDRIAL DISEASES The present invention relates to the field of medicine, in particular to the treatment of mitochondrial diseases, and more particularly to those mitochondrial diseases caused by deletions/depletion of mitochondrial DNA (mtDNA).

BACKGROUND ART

The mitochondrial genome (mtDNA) is a 16.5 kb DNA molecule that is normally present in multiple copies in individual mitochondria.

An important group of Mendelian mitochondrial diseases are caused by mutations in nuclear genes whose products are involved in mtDNA replication or maintenance. These rare disorders are also known as defects of intergenomic communication, mtDNA depletion diseases, mtDNA multiple deletions diseases, or mitochondrial depletion and deletions diseases (MDDS). These entities have specific orphan codes: ORPHA35698 for mitochondrial DNA depletion syndrome, and ORPHA254807 for multiple mitochondrial DNA deletion syndrome, and are also recognized in the OMIM database http://www.omim.org/phenotypicSeries/PS603041 for mitochondrial DNA depletion and http://www.omim.org/phenotypicSeries/PS157640 for multiple mitochondrial DNA deletions. These diseases are a complex group of genetically and clinically heterogeneous diseases characterized by the presence of mtDNA aberrations in one or a combination of affected tissues (e.g. skeletal muscle, liver, brain).

The severity and progression of these disorders is also highly variable, ranging from mild manifestations (e.g. progressive external ophthalmoplegia) to severe phenotypes that may lead to death during infancy or early childhood, as has been observed in classical mtDNA depletion syndromes.

Most genes hitherto associated with defects in intergenomic communication are either directly involved in mtDNA replication or implicated in metabolism of deoxyribonucleoside triphosphates (dNTP), the building blocks of DNA synthesis. However, an increasing number of mutations leading to MDDS is being identified in genes which are causing mtDNA instability by a pathomechanism yet unknown (OPA1, MPV17, FBXL4, etc). It has been classically considered that defects in certain genes specifically lead to either depletion or multiple mtDNA deletions. For example, DGUOK defects usually lead to mtDNA depletion, whereas OPA1 defects typically cause multiple mtDNA deletions. Nonetheless, there is growing evidence that mtDNA depletion and multiple deletions can be considered manifestations of the same pathogenic pathways affecting mtDNA replication and repair. Mutations in genes that until recently had only been associated with mtDNA depletion with infantile onset (TK2, DGUOK), have now been found to additionally cause multiple mtDNA deletions, with adult onset in some cases.

As MDDS are multi-organ disorders, a multidisciplinary team is needed, including different specialists, to provide supportive care and symptomatic treatment for the associated complications.

Up to now there have not been developed effective therapies for the treatment of these so complex diseases. This is basically due to the lack of information about the exact factors an mechanisms causing such diseases, to the variability between one syndrome and another, etc.

In spite of the above, some attempts have been made to find appropriate therapies for MDDS caused by defects in dNTP metabolism where dNTP availability is known to be compromised. For example, recent experimental studies have shown that bypassing the defective step in deoxyribonucleotide biosynthesis, mtDNA depletion can be overcome. In particular, it has been reported that addition of purine dN monophosphates (dNMPs) can rescue mtDNA depletion in TK2-KO mice [1]. Furthermore, Camara Y. et al. [2] reported that the use of deoxyribonucleosides and/or specific inhibitors of their catabolism may be an effective pharmacological approach for treating different MDDS due to defects in dNTP homeostasis.

In spite of the efforts made, there is still the need of therapeutic approaches for these and other MDDS variants.

SUMMARY OF THE INVENTION

The present inventors have found that the administration of deoxyribonucleosides allow the restoration of mtDNA levels in MDDS diseases not caused by a defect in dNTP metabolism.

So far now, there was the general thought that administration of nucleosides could only be effective in the treatment of mitochondrial diseases caused by a defect in dNTP metabolism. In fact, the prior art had postulated that a disease caused by a defect in dNTP metabolism could be overcome administering the "defected" nucleoside [2]. Therefore, up to now, it was expected that only diseases caused by a deficiency in a particular nucleotide could be treated administering a sufficient amount of the "defected" nucleotide/nucleoside in question.

Contrary to the teachings of the prior art, the present inventors have administered deoxyribonucleosides to fibroblast samples from patients previously diagnosed of MDDS carrying certain mutations affecting the catalytic subunit of polymerase gamma protein 1 (one of the enzymes involved in mtDNA replication machinery). It was surprisingly found that the administration of deoxyribonucleosides to those samples restored mtDNA levels to "normal" (healthy) levels (see Table 3, below) independently to the mutation carried by the patient. It was unpredictable that the abnormal function of POLG1 enzyme (which at the end negatively affects the correct work of the replication machinery), caused by different mutations, could be overcome administering deoxyribonucleosides for all three patient-derived cells to the same degree. It is indicative that the recovery of the mtDNA levels with the administration of deoxyribonucleosides is independent of the mutation responsible for the mtDNA replication machinery defect.

Thus, in a first aspect the present invention provides a composition comprising one or more canonical deoxyribonucleosides for use in the treatment of a mitochondrial DNA depletion and/or deletion syndrome, provided that the syndrome is not caused by a defect in the deoxyribonucleoside triphosphate (dNTP) metabolism. This aspect can also be formulated as the use of a composition comprising one or more canonical deoxyribonucleosides for the manufacture of a medicament for the treatment of a mitochondrial DNA depletion and/or deletion syndrome, provided that the syndrome is not caused by a defect in the deoxyribonucleoside triphosphate (dNTP) metabolism. This aspect can be alternatively formulated as a method of treating a mitochondrial DNA depletion and/or deletion syndrome which is not caused by a defect in the deoxyribonucleoside triphosphate (dNTP) metabolism, the method comprising administering an effective therapeutically amount of one or more canonical deoxyribonucleosides to a subject in need thereof.

Experimental data has been obtained in cells derived from patients suffering different clinical manifestations due to a deficiency in POLG.

POLG is a gene that codes for the catalytic subunit of the mitochondrial DNA polymerase, called DNA polymerase gamma. In eukaryotic cells, the mitochondrial DNA is replicated by DNA polymerase gamma, a trimeric protein complex composed of a catalytic subunit of 140 kDa encoded by the POLG gene and a dimeric accessory subunit of 55 kDa encoded by the POLG2 gene. The catalytic subunit contains three enzymatic activities, a DNA polymerase activity, a 3'-5' exonuclease activity that proofreads misincorporated nucleotides, and a 5'-dRP lyase activity required for base excision repair. In examples provided below, patients suffered from a POLG deficiency due to mutations in exonuclease or polymerase domain (R3090 (in exonuclease domain), and G848S and V1177L (in polymerase domain)) and in the linker region (W748S).

The present inventors have surprisingly found that the administration of deoxyribonucleosides "works" for all tested POLG mutants and that, independently of whether the mutation affects POLG's function or structure, there is a substantial improvement in the enzymatic activity of mutated-POLG form, in such extent that mtDNA levels are restored and are at the same order as those shown by a healthy subject. That is, the administration of deoxyribonucleosides hyperstimulates POLG enzyme form which, prior to said administration, partially lacked polymerase activity.

The experimental data provided below (summarized in Table 3 below) allow concluding that the administration of deoxyribonucleosides can be enough to accelerate mtDNA polymerization rate independently of the mutation in POLG gene. But also, these findings also suggests that any other MDDS disease, which is known to be characterized by a reduction of mtDNA (either by mtDNA copy number reduction or by multiple mtDNA deletions), and which is due to mutations in proteins either from the replication machinery itself (POLG1, POLG2, which encodes the ancillary unit of polymerase gamma; PEO1, MGME1, and DNA2, among others) or indirectly involved in mtDNA replication (such as MPV17), can also be efficiently treated by hyperstimulating POLG enzyme activity through the administration of deoxyribonucleosides: enhancing the POLG activity there is a substantial increase in mtDNA levels, which can "neutralize" the loss of mtDNA, independently of the cause of such loss (particular mutation in a particular protein), and restore a "normal" level.

Therefore, a dNs-based therapeutic strategy could thus partially or fully counteract mtDNA depletion in any defect where replication of mtDNA is challenged provided by either partially or fully active polymerase activity.

From the experimental shown below it can also be concluded that the recovery in mitochondrial DNA levels may be independent from the severity of the patient's disease, which confers a great therapeutic value to the invention.

Further advantages associated to the administration of deoxyribonucleosides in the treatment of MDDS object of the present invention are the cost (it is cheap) and that there are not special requirements for their conservation. In addition, canonical deoxyribonucleosides are natural compounds that are normally present in all living organisms.

BRIEF DESCRIPTION OF THE DRAWINGS

FIG. 1: amino acid of POLG1 protein according to NCBI database. Highlighted are the following mutations: at position 309→Arginine by a Cysteine, at position 748→Tryptophan by Serine, at position 848→Glycine by Serine, at position 1143→glutamic acid by Glycine, at position 1177→Valine by Leucine.

DETAILED DESCRIPTION OF THE INVENTION

Figure 2:
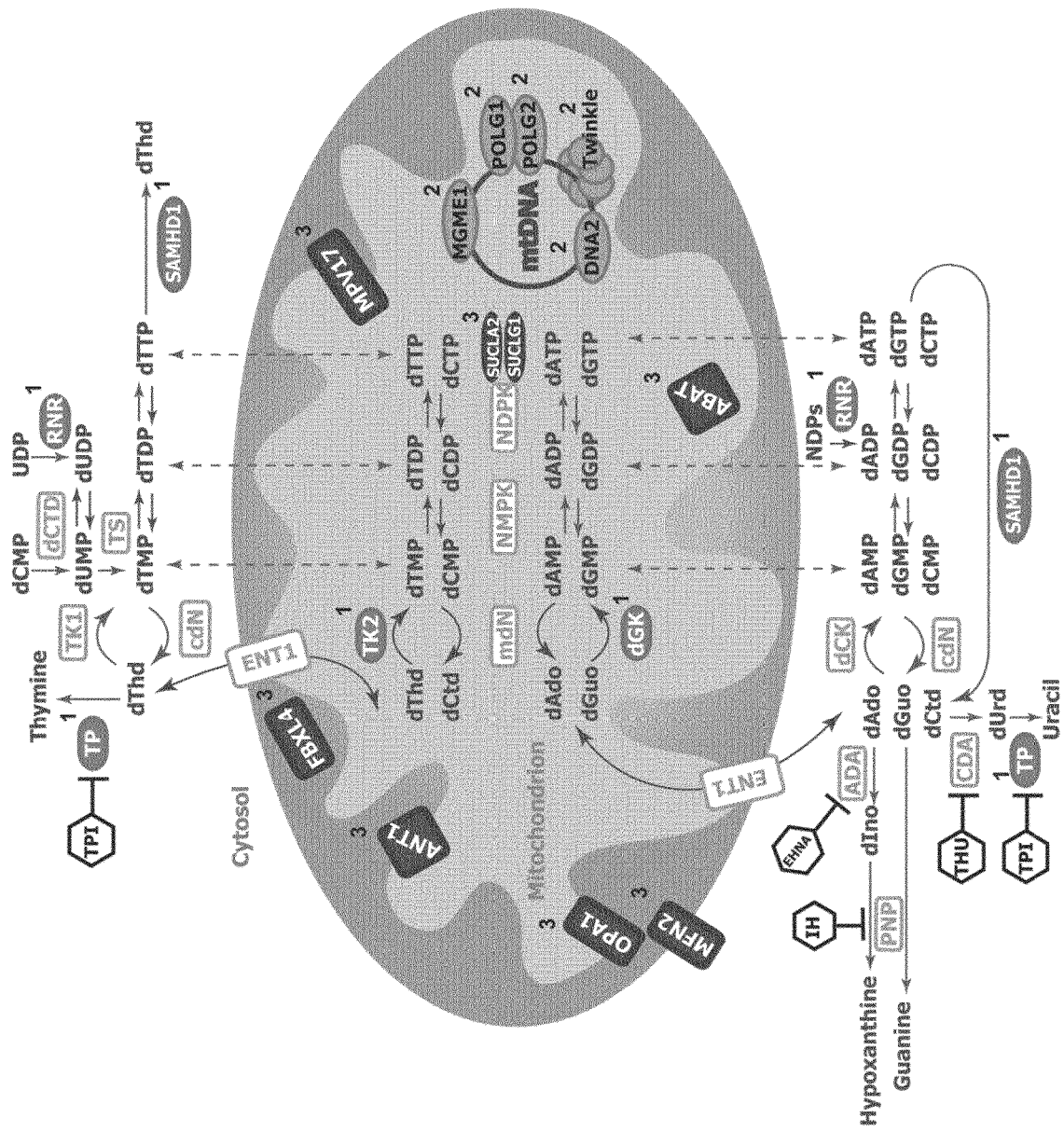
FIG. 2: Representation of the metabolic pathways involved in mtDNA depletion and deletion syndromes (MDDSs). Proteins whose dysfunction has been linked to MDDS are labelled with number 1 (involved in dNTP metabolism), with number 2 (belonging to the replication machinery) or number 3 (linked to MDDS through an unknown pathomechanism). Although an association of SUCLA2 and SUCLG1 with the nucleotide diphosphate kinase has been documented, their relationship with dNTP metabolism has not been clearly evidenced. Other proteins involved in dNTP metabolism but that had not yet been associated with MDDS and specific inhibitors of deoxyribonucleoside catabolic enzymes are also depicted: tetrahydrouridine (THU); 5-chloro-6-[1-(2-iminopyrrolidinyl) methyl] uracil hydrochloride (TPI), Immucilin H (IH) and erythro-9-(2-hydroxy-3-nonyl) adenine (EHNA). Abbreviations: ABAT: 4-aminobutyrate aminotransferase; ADA: adenosine deaminase; ANT1: Adenine nucleotide translocator 1; CDA: cytidine deaminase; cdN: cytosolic deoxyribonucleotidase; dAdo: deoxyadenosine; dCK: deoxycytidine kinase; dCTD: dCMP deaminase; dCtd: deoxycytidine; dGK: deoxyguanosine kinase; dGuo: deoxyguanosine; dIno: deoxyinosine; DNA2: DNA replication helicase 2; dThd: thymidine; dUrd: deoxyuridine; ENT1: equilibrative nucleoside transporter 1; FBXL4: F-box and leucine-rich repeat protein 4; mdN: mitochondrial deoxyribonucleotidase; MFN2: Mitofusin-2; MGME1: Mitochondrial genome maintenance exonuclease 1; MPV17: mitochondrial inner membrane MPV17; NDPK: nucleotide diphosphate kinase; NMPK: nucleotide monophosphate kinase; OPA1: Optic atrophy 1; PNP: purine nucleoside phosphorylase; POLG1: polymerase gamma subunit 1; POLG2: polymerase gamma subunit 2; RNR: ribonucleotide reductase; SAMHD1: SAM domain and HD domain-containing protein 1; SUCLA2: β-subunit, Succinate-CoA ligase; SUCLG1: α-subunit, Succinate-CoA ligase; TK1: thymidine kinase 1; TK2: thymidine kinase 2; TP: thymidine phosphorylase; TS: thymidylate synthase; Twinkle: mitochondrial Twinkle helicase.
Figure 3:
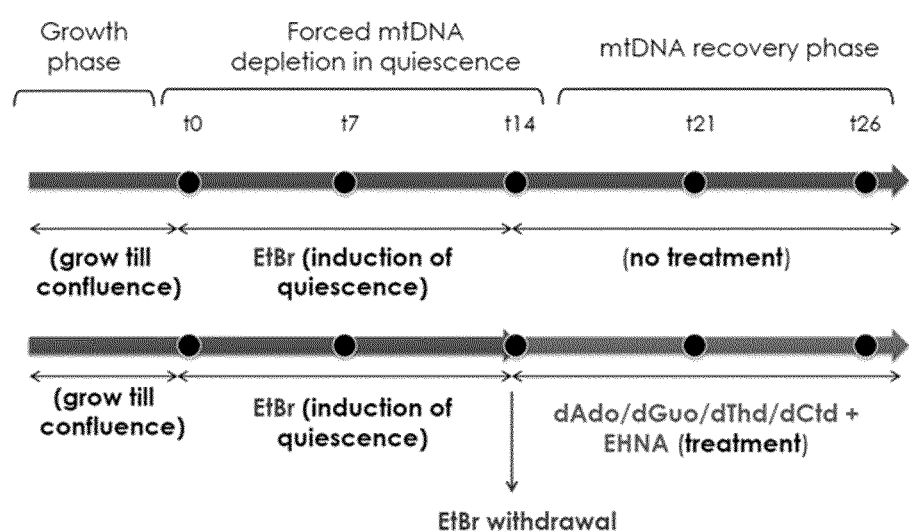
FIG. 3: Scheme of the experimental design followed for determining mtDNA levels in cells collected at the indicated times (t0, t7, t14, t21 and t26). Stability of dNs was monitored in cell media after 2-3 days of culture (t16-t17).

The present invention is based on the finding that a recovery in mtDNA levels can be achieved when deoxyribonucleosides are administered to patients suffering MDDS caused by a defect other than a defect in dNTP metabolism. Nucleosides are glycosylamines that can be thought of as nucleotides without a phosphate group. A nucleoside consists simply of a nucleobase (also termed a nitrogenous base) and a 5-carbon sugar (either ribose or deoxyribose), whereas a nucleotide is composed of a nucleobase, a five-carbon sugar, and one or more phosphate groups. In a nucleoside, the base is bound to either ribose or deoxyribose via a beta-glycosidic linkage. Examples of nucleosides include cytidine, uridine, adenosine, guanosine, thymidine and inosine.

As it has been explained above, MDDS diseases are a group of diseases caused by defects in mitochondrial DNA (mtDNA) replication and encompasses disorders characterized either by mtDNA copy number reduction (mtDNA depletion syndrome) or multiple mtDNA deletions (mtDNA deletions syndrome). They are well recognized entities in orphaned and in the Online Mendelian Inheritance in Man catalogue, which are reference sites for the skilled in these kind of pathologies.

This group of mitochondrial diseases constitutes a well-recognized group of disorders caused by mutations in a defined group of genes, and so it is well-known by the experts on mitochondrial disorders. In some cases, the name under which this group of diseases is known may be variable: mtDNA depletion and deletions syndromes [3,4]; defects of intergenomic communication (or signaling) [5]; mtDNA replication defects[6]; etc. Two or more of these names sometimes coexist in the same publication.

Diseases caused by defects in mtDNA replication can be due by mutations in:

A—Genes encoding proteins belonging to the mtDNA replication machinery (labelled with number "2" in FIG. 2)[7, 8, 9, 10, 11]

B—Genes encoding proteins participating in nucleoside/nucleotide catabolism or anabolism (labelled with number "1" in FIG. 2)[12, 13, 14, 15]

C—Genes encoding proteins with unknown function, or whose function does not belong to categories A or B and cannot be biochemically linked with mtDNA replication process (labelled with number "3" in FIG. 2).[16, 17, 18, 19, 20, 21, 22, 23, 24]

This classification has been explicitly recognized by the skilled people in the art [3, 4, 6, 25, 26, 27].

dNTPs are required at the replication fork as substrates for DNA synthesis. Mammalian cells obtain the precursors for DNA synthesis and repair from two different metabolic sources, cytosolic de novo synthesis, and salvage pathways, the latter based on two parallel set of enzymes located in cytoplasm and mitochondrial matrix. The synthesis of dNTPs is coupled to nuclear DNA replication, the moment when cell demands on DNA precursors are at their highest. The dNTPs pool is markedly reduced once the replication phase (S phase) is over, or in non-dividing cells. De novo synthesis is based on the cytosolic activity of ribonucleotide reductase (RNR) (with the exception of dTMP for which it has been recently identified a mitochondrial thymidylate synthase. RNR catalyses the allosterically balanced reduction of all four ribonucleoside diphosphates to the corresponding deoxyribonucleosides (dNs), providing the cell with high concentrations of dNTPs during the S phase of cell cycle. RNR is a heterotetramer containing two copies of a large subunit (R1) and two of a small subunit (R2 or p53R2). While R2 undergoes proteasome-dependent degradation in late-mitosis, p53R2 is present throughout the cell cycle and its expression remains stable also in non-dividing cells. Differently to nuclear genome replication, mtDNA synthesis occurs independently from cell division. Although cytosolic de novo synthesis supported by p53R2 is much lower compared to that provided by R2 during S phase, it has been proved to be essential to mtDNA maintenance since mutations on p53R2 gene lead to mtDNA depletion.

The salvage synthesis pathway is based on the sequential phosphoryation of the precursor nucleosides to dNMPs, dNDPs and ultimately dNTPs. The first and rate-limiting step in this pathway is irreversibly catalysed by the deoxynucleoside kinases. Thymidine kinase 1 (TK1) and deoxycytidine kinase (dCK) operating in the cytosol, while thymidine kinase 2 (TK2) and deoxyguanosine kinase (dGK) localize within mitochondria. Mutations on the mitochondrial kinases participating in salvage pathway, cause severe MDDS evidencing mitochondrial dependence on salvage supply of dNTPs for its DNA maintenance and repair. Additional nucleotide kinases complete the phosphorylation of all four dNMPs to the final corresponding dNTPs needed for DNA synthesis. Cytosol and mitochondrial matrix are independent compartments but they actively communicate, bidirectionally exchanging pool components across the inner mitochondrial membrane through carriers that are to date, poorly characterized. As a consequence of this crosstalk, changes in dNTPs pool sizes are believed to occur in parallel in both compartments. Therefore mitochondria become more vulnerable to defects on their own salvage supply of dNTPs in post-mitotic cells, where the cytosolic pool has been largely diminished.

The dNTP pool size depends on the balance between the anabolic pathways mentioned above, the rate of incorporation to DNA and the catabolic processes responsible for dNTPs degradation.

dNTPs are required at the replication fork as substrates to be incorporated into DNA by mitochondrial polymerase gamma (POLG). Though the exact mode of mtDNA replication is currently under debate, the basic mitochondrial replisome, formed by the polymerase gamma (constituted by a catalytic subunit encoded by POLG1 and two accessory subunits encoded by POLG2), Twinkle helicase and the single-stranded-binding (SSB) protein has been reconstituted in vitro[28]. Additional not-fully characterized activities are required for full in vivo replication of the mtDNA molecule (e.g. primase, topoisomerase) and for the initiation and regulation of the process in response to different stimuli and stress. Some examples are MGME1 and DNA2 genes that encode proteins participating at some level in the replicative process (maturation of 7S RNA, helicase activity respectively) and which mutations have been recently associated with MDDS.

In one embodiment, the treatment of the syndrome is achieved by increasing polymerase gamma activity.

In one embodiment, the one or more deoxyribonucleosides are canonical deoxyribonucleosides. Advantageously, with such deoxyribonucleosides the onset of effect can be got earlier because no extra-processing of the metabolite is needed. In addition, since canonical deoxyribonucleosides are substantially identical to endogen deoxyribonucleosides, there can be a reduction in the risk of the side-effects associated to the treatment of this disease.

In one embodiment of the first aspect of the invention, the syndrome is due to a defect in the mitochondrial DNA replication machinery.

In another embodiment of the first aspect of the invention the defect is due to one or more mutations in one or more proteins of the mitochondrial DNA replication machinery.

In still another embodiment the protein is selected from the group consisting of: DNA polymerase subunit gamma-1 (POLG1), DNA polymerase subunit gamma-2 (POLG2), Twinkle protein (PEO1), mitochondrial genome maintenance exonuclease 1 (MGME1), and human helicase/nuclease DNA 2 protein. In another embodiment the protein is the DNA polymerase subunit gamma-1 (POLG1) or Twinkle protein.

Polymerase gamma is a heterotrimer constituted by one catalytic subunit (encoded by POLG1) and two accessory subunits that act as processivity factors and modulators of DNA binding (encoded by POLG2). Its accession number in NCBI database is NP_001119603.1 (also provided as FIG. 1, and SEQ ID NO: 1).

POLG-related disorders present a continuum of broad and overlapping phenotypes presenting from early childhood to late adulthood. The clinical phenotypes of POLG-related disorders include autosomal recessive and dominant adult-onset PEO, myoclonic epilepsy, myopathy, sensory ataxia (MEMSA) syndrome, ataxia-neuropathy spectrum including mitochondrial recessive ataxia syndrome (MIRAS), and sensory ataxia, neuropathy, dysarthria, ophthalmoplegia (SANDO) syndrome, and hepatocerebral MDS (Alpers-Huttenlocher syndrome). More recently, POLG mutations were identified in individuals with clinical features of MNGIE, but no leukoencephalopathy.

The incidence of Alpers-Huttenlocher syndrome has been estimated to be ~1:50,000. It is the most severe phenotype associated with POLG mutations and characterized by a progressive encephalopathy with intractable epilepsy and psychomotor delay, neuropathy, and hepatic failure. Affected individuals usually present between the age of 2 and 4 years with seizures (focal, generalized, myoclonic, epilepsia partialis continua, or status epilepticus), headaches that are typically associated with visual sensations or visual auras, hypotonia, and psychomotor regression. Early in the disease course areflexia and hypotonia are present and later followed by spastic paraparesis that evolves over months to years, leading to psychomotor regression. Affected individuals develop liver dysfunction with elevated transaminases, hypoalbuminemia, coagulopathy, hypoglycemia, and hyperammonemia. Liver involvement can progress rapidly to endstage liver failure within a few months. CSF protein is generally elevated. Neuroimaging may show gliosis and generalized brain atrophy. Liver histology may demonstrate macro- and microvesicular steatosis, centrilobular necrosis, fibrosis, cirrhosis, bile duct proliferation, and mitochondrial proliferation. mtDNA content is reduced in liver. Disease progression is variable, with life expectancy from onset of symptoms ranging from 3 months to 12 years.

In one embodiment, the mitochondrial DNA depletion and/or deletion syndrome is caused by a defect in the mitochondrial replication pathway, said defect being due to one or more of the following mutations in POLG1 protein: mutation at position 309 of an Arginine by a Cysteine [29], mutation at position 748 of a Tryptofan residue by Serine (rs113994097), mutation at position 848 of a Glycine by Serine (rs113994098), mutation at position 1143 of a glutamic acid by Glycine (rs2307441), and a mutation at position 1177 of a Valine by Leucine.

Alternatively, in another embodiment of the first aspect of the invention the defect is due to one or more mutations in one or more proteins selected from the group consisting of: ANT1, MPV17, SUCLA2, FBXL4, ABAT, SUCLG1, MFN2, and OPA1. In another embodiment of the first aspect the defect is due to one or more mutations in a protein selected from the group consisting of: OPA1, SUCLA2, and SUCLG1.

In another embodiment, the one or more deoxyribonucleosides are canonical deoxyribonucleosides. In another embodiment the one or more deoxyribonucleosides are selected from the group consisting of: deoxyadenosine, deoxyguanosine, deoxycytidine, and deoxythymidine. In still another embodiment, the composition comprises four canonical deoxyribonucleosides. In still another embodiment, the composition comprises four canonical deoxyribonucleosides and does not contain any further nucleoside (which means that the composition uniquely comprises as "deoxyribonucleoside component" these four deoxyribonucleosides but can include excipients, carriers, etc.) In still another embodiment, the composition comprises deoxyadenosine, deoxythimidine, deoxycytidine, and deoxyguanosine. In still another embodiment, the composition comprises deoxyadenosine, deoxythimidine, deoxycytidine, and deoxyguanosine and does not contain any further nucleoside (which means that the composition uniquely comprises as "nucleoside component" these four nucleosides but can include excipients, carriers, etc).

The skilled in the art is able to determine the amount of each one of the deoxyribonucleosides to restore mtDNA levels (i.e., the therapeutically effective amount to ameliorate signs and symptoms of mitochondrial disorders). In another embodiment, when the composition comprises more than one canonical deoxyribonucleoside, the nucleosides are present in an equimolar ratio.

In one embodiment, the composition comprises a combination consisting of deoxyadenosine (dAdo), deoxycytidine (dCtd), deoxyguanosine (dGuo), and deoxythymidine (usually named as thymidine, dThd), being all nucleosides in equimolar ratio.

In another embodiment the composition further comprises one or more pharmaceutically acceptable inhibitors of nucleoside degradation.

There are well-known inhibitors of nucleoside degradation in the state of the art. Illustrative non-limitative examples are: Inmucilin H or Forodesine, as inhibitors of dGuo degradation, Tetrahydrouridine as inhibitor of dCtd degradation, 5-chloro-6-[1-(2-iminopyrrolidinyl) methyl] uracil hydrochloride (TPI) as inhibitor of dThd degradation, and erythro-9-(2-hydroxy-3-nonyl)adenine (EHNA) as inhibitor of dAdo degradation. FIG. 1 shows the mode of action of these inhibitors.

The skilled in the art is able to determine the amount of inhibitor(s) needed to guarantee the bioavailability of the nucleoside(s) for restoring mtDNA levels.

In one embodiment the composition further comprises one pharmaceutically acceptable inhibitor of the degradation of nucleoside. In another embodiment the pharmaceutically acceptable inhibitor is an inhibitor of deoxyadenosine degradation. In another embodiment the inhibitor is erythro-9-(2-hydroxy-3-nonyl)adenine (EHNA).

The active components described for use herein can be formulated with pharmaceutically suitable excipients or carriers, selected to render such compositions amenable to delivery by oral, rectal, parenteral (e.g., intravenous, intramuscular, intraarterial, intraperitoneal, and the like), or inhalation routes, osmotic pump, topical, opthalmic, and the like.

Ointments are semi-solid preparations that consist of the active ingredient incorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

In addition to the topical method of administration described above, there are various methods of administering the compounds of the present invention systemically. One such means would involve an aerosol suspension of respirable particles comprised of the active compound, which the subject inhales. The active compound would be absorbed into the bloodstream via the lungs and contact the systemic circulation in a pharmaceutically effective amount. The respirable particles may be liquid or solid, with a particle size sufficiently small to pass through the mouth and larynx upon inhalation.

Another means of systemically administering the active compounds to the subject would involve administering a liquid/liquid suspension in the form of nasal drops of a liquid formulation, or a nasal spray of respirable particles which the subject inhales. Liquid pharmaceutical compositions of the active compound for producing a nasal spray or nasal drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I, are in the form of a solid, a solution, an emulsion, a dispersion, a micelle, a liposome, and the like, wherein the resulting formulation contains the active compounds contemplated for use herein, in admixture with an organic or inorganic carrier or excipient suitable for nasal, enteral or parenteral applications. The active ingredients may be compounded, for example, with the usual non-toxic, pharmaceutically or physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used. The active compounds contemplated for use herein are included in the pharmaceutical formulation in an amount sufficient to produce the desired effect upon administration (i.e., a therapeutically effective amount).

The powder, solution, suspension, or tablet contains the active compound in a physiologically compatible vehicle, as those skilled in the art of oral delivery system development can select using conventional criteria. For example, such formulations may contain one or more agents selected from flavoring agents (such as peppermint, oil of wintergreen or cherry), coloring agents, preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, olive oil, and the like.

Additional means of systemic administration of the active compound to the subject would involve a suppository form of the active compound, such that a therapeutically effective amount of the compound reaches the systemic circulation.

Depending on the solubility of the particular formulation of active compound administered, the daily dose to ameliorate signs and symptoms of mitochondrial disorders may be divided among one or several unit dose administrations.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Methods

Patients

Cells derived from three patients suffering from POLG deficiency were included in the study. All subjects gave informed consent in accordance with our Institutional Review Boards and the Declaration of Helsinki. Mutations in POLG (RefSeq NP_001119603.1) were identified in all 3 patients by Sanger sequencing. Total DNA was isolated from fibroblasts with the QiaAMP Mini (Qiagen) and fragments of approximately 500 bp including the mutation site of interest were amplified by conventional PCR with the following primer pairs listed below and rTaq (Takara):

The primers used were:

```
Primers 1 (R3090, 925 c → t)
                                  (SEQ ID NO: 2)
Forward Primer GTCCACACCACCAAGCAGT (SEQ ID NO: 3)
Reverse Primer GGTCCCAAGCACTATGCTCC Primers 2 (W7485 c. 2243G → C)
                                  (SEQ ID NO: 4)
Forward Primer CCTTGCTGAATGCAGGTGCT (SEQ ID NO: 5)
Reverse Primer TGTGCCTGAAATCACACTCTGT Primers 3 (G8485 c. 2542G → A)
                                  (SEQ ID NO: 6)
Forward Primer ATGGTCTGCTGAGTGGTTGT (SEQ ID NO: 7)
Reverse Primer CCCTCAGAGCCCAGTTTCTAC Primers 3 (E1143G c. 3428A → G)
                                  (SEQ ID NO: 8)
Forward Primer CCCAGTTTATGACCAGCCGT (SEQ ID NO: 9)
Reverse Primer CAAGGAACGCTCACCCAAAG
```

-continued

```
Primers 4 (V1177L c.3529G → C)
                                            (SEQ ID NO: 10)
Forward Primer AGGGGAAGCCCTGCTCTAAG (SEQ ID NO: 11)
Reverse Primer ACAAATGTGTTGTGCTCACCC
```

Sequencing reactions were carried out with the same primers and BigDye v3.1 sequencing kit (Life Technologies), purified by BigDye X-Terminator purification kit (Life Technologies) and sequenced in an ABI 3130 sequencer (Applied Biosystems). Patient 1 (homozygous for the p.R309C mutation) suffered from a severe neurological phenotype (neuropathy, encephalopathy, MNGIE-like) that lead to death at age 20; patient 2 (compound heterozygote for the p.W748S and p.G848S mutations) suffered a less severe phenotype but also predominantly neurological (neuropathy, psychiatric symptoms, MNGIE-like); patient 3 (heterozygote for two dominant aminoacid changes in cis p.V1177L and p.E1143G) presented a familiar pattern of dominant inheritance of PEO (progressive external ophthalmoplegia), psychiatric symptoms and proximal muscle weakness. Skeletal muscle from all three patients evidenced accumulation of mtDNA deletions but no significant depletion.

Cell Culture

Primary cultured fibroblasts were obtained from skin biopsies of patients 1-3 and 4 healthy donors. All subjects gave informed consent in accordance with our Institutional Review Boards and the Declaration of Helsinki.

Cells were seeded in 6-well plates of 9.5 cm$^2$ in Dulbecco's modified Eagle's medium (DMEM) with 4.5 g/L glucose, supplemented with 2 mM L-glutamine, 100 U/mL penicillin and streptomycin, and 10% dialyzed Fetal Bovine Serum (FBS) (Invitrogen) in a humidified incubator at 37° C. and 5% $CO_2$. After tight confluence was reached, FBS was reduced to 0.1% to induce quiescence and simultaneous treatment with 5 ng/ml of EtBr (ethidium bromide, Merck) was initiated (day 0, t0). Cell media was replaced with the same treatment every 2-3 days for two weeks. At day 14 (t14) EtBr was withdrawn from cell media and the treatment of a set of all cells was initiated with 200 µM of all four deoxynucleosides (dNs): dAdo (deoxyadenosine, Sigma), dCtd (deoxycytidine, Sigma), dGuo (deoxyguanosine, Sigma), dThd (deoxythymidine, Sigma) and 5 µM EHNA (Sigma). A set of cells was left untreated and all parameters were monitored in parallel. Cell media was replaced with the same treatment every 2-3 days for 12 additional days. At days 16 or 17 media were collected and stored at −20° C. until further use. For DNA analysis, cells were harvested at days 0, 7, 14, 21 and 26 by trypsinization, washed with phosphate-buffered saline, pelleted and stored at −20° C. until DNA isolation (FIG. 2). Total DNA was isolated using the QiaAMP DNA mini kit (Qiagen).

Assessment of Deoxynucleosides Stability in Cell Culture Medium dNs and some related metabolites were measured by liquid chromatography coupled to tandem mass spectrometry (LC-MS/MS), using an Acquity UPLC-MS/MS apparatus (Acquity UPLC-Xevo™ TQ Mass Spectrometer, Waters, Milford, Mass.), as previously described [2]. Cell medium was deproteinized by ultrafiltration (3 kDa Amicon Ultra filters, Millipore) at 14,000×g and 4° C. for 30 min before injection in the LC-MS/MS system.

mtDNA Investigations mtDNA copy number was assessed by quantitative PCR as previously described [2].

mtDNA deletions were investigated by long-range PCR blot following the PCR conditions and primers disclosed in Nishigaki et al.[30]:

```
Primer forward (F1142-1516):
                                            (SEQ ID NO: 12)
ACCGCCCGTCACCCTCCTCAAGTATACTTCAAAGG Primer reverse (R1180-1146):
                                            (SEQ ID NO: 13)
ACCGCCAGGTCCTTTGAGTTTTAAGCTGTGGCTCG
```

2. Results

EtBr Exposure Induces a Larger mtDNA Depletion in POLG-Deficient Quiescent Fibroblasts An important limitation when testing potential treatments for mtDNA depletion is the fact that in many cases, MDDS-patient-derived cells do not show any mtDNA abnormalities in cell culture. For this reason, different models have been developed in order to demonstrate molecular defects affecting mtDNA replication. EtBr exposure has been repeatedly used in the state of the art to force mtDNA depletion in cultured cells and to analyse their replicative ability to recover normal mtDNA levels (Pontarin et al. "Mammalian ribonucleotide reductase subunit p53R2 is required for mitochondrial DNA replication and DNA repair in quiescent cells", 2012, PNAS, v. 109(33), pages 13302-13307). mtDNA depletion was induced both in healthy controls and in POLG-deficient quiescent cells by 14 days exposure to 5 ng/ml EtBr. It was observed a marked mtDNA depletion in all cells. However, all POLG-deficient cells experienced a higher degree of mtDNA depletion compared to that observed in fibroblast lines obtained from healthy controls (averaged percentage of mtDNA residual levels±SE: 17.5±2.3%; in control cells: 39.68±6.6%). This data suggests that the molecular defect caused by POLG mutations could aggravate EtBr interference with the replication process.

POLG-Deficient Fibroblasts Fully Recover mtDNA Levels after EtBr-Forced Depletion when Treated with a Combination of dNs Plus EHNA After EtBr withdrawal, the effect that supplementation of cell culture media with all four dNs would have on recovery of mtDNA levels was studied. It was previously reported that dAdo was especially sensitive to extracellular and intracellular enzymatic degradation, mainly by ADA (adenosine deaminase) [2]. Thus, the media was supplemented with an equimolar concentration of all four canonical dNs (200 µM dGuo, dAdo, dThd and dCtd) plus 5 µM EHNA (Sigma) in order to exert a partial inhibition of dAdo catabolism and improve its stability. At days 16-17 the concentration of the added dNs was measured and some of their derived metabolites in 2-3-days conditioned media, following the same protocol as the one disclosed in Cámara Y. et al., 2014[2]. Despite partial degradation, concentration of all dNs remained in all cases above 70% of that initially added (Table 2). No significant differences in dNs stability were observed between conditioned media from control or patient-derived cells.

TABLE 2

Compound concentration in media after 2-3 days of treatment

|  | Controls | Patients |
|---|---|---|
| dCtd | 168.9 ± 27.4 | 196 ± 24.0 |
| dUrd | 46.7 ± 27.6 | 6.2 ± 3.4 |
| dThd | 154.8 ± 9.1 | 153.9 ± 10.2 |
| Thymine | 48.4 ± 17.3 | 36.4 ± 10.2 |
| dGuo | 171.6 ± 17.9 | 173.3 ± 16.5 |
| Guanine | 71.0 ± 27.5 | 57.9 ± 12.1 |
| dAdo | 140.4 ± 15.7 | 142.9 ± 17.5 |
| dIno | 50.7 ± 22.1 | 30.7 ± 10.7 |
| hypoxanthine | 23.7 ± 8.8 | 22.7 ± 8.3 |

Results are mean ± SD from three different POLG-deficient and four control cell lines.
dUrd: deoxyuridine; dIno: deoxyinosine.

mtDNA recovery was monitored prior and after EtBr withdrawal either in the presence or absence of dNs supplementation (following the same protocol as the one of Camara Y. et al., 2014[2]). mtDNA copy number from control cells reached values above 100% of initial levels 12 days after EtBr withdrawal regardless of dNs treatment (averaged percentage of mtDNA residual levels±SE: 129.8±35.2% without treatment; 153.9±40.6% with treatment). Conversely, POLG-deficient cells were unable to recover normal mtDNA levels (26.6±1.5%) unless being supplemented with dNs.

TABLE 3 mtDNA levels in quiescent fibroblasts at different time points during the experiment.

A

| day | control 1 w/o treatment | control 1 with treatment | control 2 w/o treatment | control 2 with treatment | control 3 w/o treatment | control 3 with treatment | control 4 w/o treatment | control 4 with treatment |
|---|---|---|---|---|---|---|---|---|
| 0 | 100.0 | | 100.0 | | 100.0 | | 100.0 | |
| 7 | 69.6 | | 53.9 | | 45.4 | | 44.6 | |
| 14 | 28.4 | | 58.8 | | 35.3 | | 36.0 | |
| 21 | 63.7 | 65.0 | 244.1 | 261.3 | 74.2 | 73.9 | 71.3 | 124.3 |
| 26 | 92.7 | 92.5 | 235.4 | 257.4 | 92.0 | 85.9 | 99.0 | 179.9 |

B

| day | patient 1 w/o treatment | patient 1 with treatment | patient 2 w/o treatment | patient 2 with treatment | patient 3 w/o treatment | patient 3 with treatment |
|---|---|---|---|---|---|---|
| 0 | 100.0 | | 100.0 | | 100.0 | |
| 7 | 77.3 | | 44.3 | | 48.6 | |
| 14 | 22.0 | | 15.4 | | 15.0 | |
| 21 | 18.3 | 116.3 | 22.4 | 48.8 | 18.9 | 40.5 |
| 26 | 28.4 | 193.1 | 27.7 | 137.2 | 23.7 | 120.6 |

Values are expressed as the percentage of mtDNA copy number respect to that at day 0. After EtBr-induced depletion cells are treated or not with dNs + EHNA from experimental day 14.

The results shown in Table 3 allow concluding that the administration of canonical nucleosides allows achieving mtDNA levels in MDDS patients comparable to those found in healthy subjects (150.3±21.9%, Table 3). Therefore, this data is indicative that the administration of nucleosides can restore mtDNA levels in patients suffering from MDDS caused by a defect other than one in dNTP metabolic defect, up to levels associated with a "healthy" condition, which is indicative of the therapeutic potential of the combination in the treatment of this kind of diseases.

REFERENCES CITED IN THE APPLICATION

1. Garone C, Garcia-Diaz B, Emmanuele V, Lopez L C, Tadesse S, et al. (2014) Deoxypyrimidine monophosphate bypass therapy for thymidine kinase 2 deficiency. EMBO Mol Med 6: 1016-1027.
2. Camara Y, Gonzalez-Vioque E, Scarpelli M, Torres-Torronteras J, Caballero A, et al. (2014) Administration of deoxyribonucleosides or inhibition of their catabolism as a pharmacological approach for mitochondrial DNA depletion syndrome. Hum Mol Genet 23: 2459-2467.
3. Camara Y, Gonzalez-Vioque E, Scarpelli M, Torres-Torronteras J, Marti R (2013) Feeding the deoxyribonucleoside salvage pathway to rescue mitochondrial DNA. Drug Discov Today 18: 950-957.
4. Suomalainen A, Isohanni P (2010) Mitochondrial DNA depletion syndromes—many genes, common mechanisms. Neuromuscul Disord 20: 429-437.
5. Spinazzola A, Zeviani M (2005) Disorders of nuclear-mitochondrial intergenomic signaling. Gene 354: 162-168.
6. Copeland W C (2012) Defects in mitochondrial DNA replication and human disease. Crit Rev Biochem Mol Biol 47: 64-74.
7. Naviaux R K, Nyhan W L, Barshop B A, Poulton J, Markusic D, et al. (1999) Mitochondrial DNA polymerase gamma deficiency and mtDNA depletion in a child with Alpers' syndrome. Ann Neurol 45: 54-58.
8. Hakonen A H, Isohanni P, Paetau A, Herva R, Suomalainen A, et al. (2007) Recessive Twinkle mutations in early onset encephalopathy with mtDNA depletion. Brain 130: 3032-3040.
9. Kornblum C, Nicholls T J, Haack T B, Scholer S, Peeva V, et al. (2013) Loss-of-function mutations in MGME1 impair mtDNA replication and cause multisystemic mitochondrial disease. Nat Genet.
10. Ronchi D, Di Fonzo A, Lin W, Bordoni A, Liu C, et al. (2013) Mutations in DNA2 Link Progressive Myopathy to Mitochondrial DNA Instability. Am J Hum Genet.

11. Longley M J, Clark S, Yu Wai Man C, Hudson G, Durham S E, et al. (2006) Mutant POLG2 disrupts DNA polymerase gamma subunits and causes progressive external ophthalmoplegia. Am J Hum Genet 78: 1026-1034.
12. Mandel H, Szargel R, Labay V, Elpeleg O, Saada A, et al. (2001) The deoxyguanosine kinase gene is mutated in individuals with depleted hepatocerebral mitochondrial DNA. Nat Genet 29: 337-341.
13. Saada A, Shaag A, Mandel H, Nevo Y, Eriksson S, et al. (2001) Mutant mitochondrial thymidine kinase in mitochondrial DNA depletion myopathy. Nat Genet 29: 342-344.
14. Bourdon A, Minai L, Serre V, Jais J P, Sarzi E, et al. (2007) Mutation of RRM2B, encoding p53-controlled ribonucleotide reductase (p53R2), causes severe mitochondrial DNA depletion. Nat Genet 39: 776-780.
15. Nishino I, Spinazzola A, Hirano M (1999) Thymidine phosphorylase gene mutations in MNGIE, a human mitochondrial disorder. Science 283: 689-692.
16. Rouzier C, Bannwarth S, Chaussenot A, Chevrollier A, Verschueren A, et al. (2012) The MFN2 gene is responsible for mitochondrial DNA instability and optic atrophy 'plus' phenotype. Brain 135: 23-34.
17. Renaldo F, Amati-Bonneau P, Slama A, Romana C, Forin V, et al. (2012) MFN2, a new gene responsible for mitochondrial DNA depletion. Brain.
18. Ostergaard E, Schwartz M, Batbayli M, Christensen E, Hjalmarson O, et al. (2005) A novel missense mutation in SUCLG1 associated with mitochondrial DNA depletion, encephalomyopathic form, with methylmalonic aciduria. Eur J Pediatr 169: 201-205.
19. Amati-Bonneau P, Valentino M L, Reynier P, Gallardo M E, Bornstein B, et al. (2008) OPA1 mutations induce mitochondrial DNA instability and optic atrophy 'plus' phenotypes. Brain 131: 338-351.
20. Blakely E L, Butterworth A, Hadden R D, Bodi I, He L, et al. (2012) MPV17 mutation causes neuropathy and leukoencephalopathy with multiple mtDNA deletions in muscle. Neuromuscul Disord 22: 587-591.
21. Spinazzola A, Viscomi C, Fernandez-Vizarra E, Carrara F, D'Adamo P, et al. (2006) MPV17 encodes an inner mitochondrial membrane protein and is mutated in infantile hepatic mitochondrial DNA depletion. Nat Genet 38: 570-575.
22. Wedding I M, Koht J, Tran G T, Misceo D, Selmer K K, et al. (2014) Spastic paraplegia type 7 is associated with multiple mitochondrial DNA deletions. PLoS One 9: e86340.
23. Bonnen P E, Yarham J W, Besse A, Wu P, Faqeih E A, et al. (2013) Mutations in FBXL4 cause mitochondrial encephalopathy and a disorder of mitochondrial DNA maintenance. Am J Hum Genet 93: 471-481
24. Gai X, Ghezzi D, Johnson M A, Biagosch C A, Shamseldin H E, et al. (2013) Mutations in FBXL4, encoding a mitochondrial protein, cause early-onset mitochondrial encephalomyopathy. Am J Hum Genet 93: 482-495
25. Nogueira C, Almeida L S, Nesti C, Pezzini I, Videira A, et al. (2014) Syndromes associated with mitochondrial DNA depletion. Ital J Pediatr 40: 34.
26. Copeland W C (2008) Inherited mitochondrial diseases of DNA replication. Annu Rev Med 59: 131-146.
27. Copeland W C (2014) Defects of mitochondrial DNA replication. J Child Neurol 29: 1216-1224.
28. Korhonen J A, Pham X H, Pellegrini M, Falkenberg M (2004) Reconstitution of a minimal mtDNA replisome in vitro. Embo J 23: 2423-2429.
29. Amiot A, Tchkiviladze M, Joly F, Slama A, Hatem D C, et al. (2009) Frequency of mitochondrial defects in patients with chronic intestinal pseudo-obstruction. Gastroenterology 137: 101-109.
30. Nishigaki Y, Marti R, Hirano M (2004) ND5 is a hot-spot for multiple atypical mitochondrial DNA deletions in mitochondrial neurogastrointestinal encephalomyopathy. Hum Mol Genet 13: 91-101.

The invention claimed is:

1. A method for the treatment of a mitochondrial DNA depletion and/or deletion syndrome due to one or more mutations in the DNA polymerase subunit gamma-1 (POLG1) protein, comprising the step of administering a therapeutically effective amount of a composition comprising deoxyadenosine, deoxyguanosine, deoxycytidine, and deoxythymidine, and optionally one or more pharmaceutically acceptable inhibitors of deoxynucleoside degradation, to a subject in need thereof, thereby treating the mitochondrial DNA depletion and/or deletion syndrome due to one or more mutations in the POLG1 protein.

2. The method according to claim 1, wherein the composition comprises one or more pharmaceutically acceptable inhibitors of degradation of deoxynucleosides.

3. The method according to claim 1, wherein the one or more mutations are selected from the group consisting of R309C, W748S, V1177L, G848S, E1143, and E1143G or combinations thereof, the positions being referred with respect to SEQ ID NO: 1.

4. The method according to claim 1, wherein the composition does not contain any further nucleoside.

5. The method according to claim 2, wherein the pharmaceutically acceptable inhibitor is an inhibitor of deoxyadenosine degradation.

6. The method of claim 5, wherein the inhibitor of deoxyadenosine degradation is erythro-9-(2-hydroxy-3-nonyl)adenine (EHNA).

7. The method of claim 1, wherein the one or more mutations in the POLG1 protein are located in the POLG1 exonuclease domain, the polymerase domain, the linker region or combinations thereof.

8. The method of claim 7, wherein the one or more mutations in the POLG1 protein are located in the POLG1 exonuclease domain.

9. The method of claim 7, wherein the one or more mutations in the POLG1 protein are located in the POLG1 polymerase domain.

10. The method of claim 7, wherein the one or more mutations in the POLG1 protein are located in the POLG1 linker region.

11. The method of claim 1, wherein the treating comprises acceleration in the subject's mtDNA polymerization rate.

12. The method of claim 1, wherein the subject has a clinical phenotype selected from the group consisting of autosomal recessive and dominant adult-onset PEO, myoclonic epilepsy, myopathy, sensory ataxia (MEMSA) syndrome, ataxia-neuropathy spectrum including mitochondrial recessive ataxia syndrome (MIRAS), and sensory ataxia, neuropathy, dysarthria, ophthalmoplegia (SANDO) syndrome, and hepatocerebral MDS (Alpers-Huttenlocher syndrome) or features of MNGIE in the absence of leukoencephalopathy.

13. The method of claim 1, wherein the subject has Alpers-Huttenlocher syndrome.

14. The method of claim 1, wherein the deoxyadenosine, deoxyguanosine, deoxycytidine, and deoxythymidine are present in the composition in an equimolar ratio.

15. The method of claim 1, wherein the composition further comprises one or more pharmaceutically acceptable excipients or carriers.

16. The method of claim 1, wherein the composition is formulated for delivery by a method selected from the group consisting of oral delivery, rectal delivery, parenteral delivery, delivery by inhalation, topical delivery or ophthalmic delivery.

17. A method of increasing mtDNA levels in vivo, comprising administering a composition comprising deoxyadenosine, deoxyguanosine, deoxycytidine, and deoxythymidine, and optionally one or more pharmaceutically acceptable inhibitors of nucleoside degradation, to a cell having one or more mutations in the POLG1 protein, thereby increasing the mtDNA level in vivo.

* * * * *

SEQUENCE LISTING

<160> NUMBER OF SEQ ID NOS: 13

<210> SEQ ID NO 1
<211> LENGTH: 1190
<212> TYPE: PRT
<213> ORGANISM: Homo sapiens

<400> SEQUENCE: 1

```
Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Ser Val Pro Ala
            20                  25                  30

Ser Asp Pro Ser Asp Gly Gln Arg Arg Gln Gln Gln Gln Gln
        35                  40                  45

Gln Gln Gln Gln Gln Gln Gln Pro Gln Gln Pro Gln Val Leu Ser Ser
    50                  55                  60

Glu Gly Gly Gln Leu Arg His Asn Pro Leu Asp Ile Gln Met Leu Ser
65              70                  75                  80

Arg Gly Leu His Glu Gln Ile Phe Gly Gln Gly Gly Glu Met Pro Gly
                85                  90                  95

Glu Ala Ala Val Arg Arg Ser Val Glu His Leu Gln Lys His Gly Leu
            100                 105                 110
```

```
Trp Gly Gln Pro Ala Val Pro Leu Pro Asp Val Glu Leu Arg Leu Pro
            115                 120                 125

Pro Leu Tyr Gly Asp Asn Leu Asp Gln His Phe Arg Leu Leu Ala Gln
        130                 135                 140

Lys Gln Ser Leu Pro Tyr Leu Glu Ala Ala Asn Leu Leu Leu Gln Ala
145                 150                 155                 160

Gln Leu Pro Pro Lys Pro Pro Ala Trp Ala Trp Ala Glu Gly Trp Thr
                    165                 170                 175

Arg Tyr Gly Pro Glu Gly Glu Ala Val Pro Val Ala Ile Pro Glu Glu
                180                 185                 190

Arg Ala Leu Val Phe Asp Val Glu Val Cys Leu Ala Glu Gly Thr Cys
            195                 200                 205

Pro Thr Leu Ala Val Ala Ile Ser Pro Ser Ala Trp Tyr Ser Trp Cys
        210                 215                 220

Ser Gln Arg Leu Val Glu Glu Arg Tyr Ser Trp Thr Ser Gln Leu Ser
225                 230                 235                 240

Pro Ala Asp Leu Ile Pro Leu Glu Val Pro Thr Gly Ala Ser Ser Pro
                    245                 250                 255

Thr Gln Arg Asp Trp Gln Glu Gln Leu Val Val Gly His Asn Val Ser
                260                 265                 270

Phe Asp Arg Ala His Ile Arg Glu Gln Tyr Leu Ile Gln Gly Ser Arg
            275                 280                 285

Met Arg Phe Leu Asp Thr Met Ser Met His Met Ala Ile Ser Gly Leu
        290                 295                 300

Ser Ser Phe Gln Arg Ser Leu Trp Ile Ala Ala Lys Gln Gly Lys His
305                 310                 315                 320

Lys Val Gln Pro Pro Thr Lys Gln Gly Gln Lys Ser Gln Arg Lys Ala
                    325                 330                 335

Arg Arg Gly Pro Ala Ile Ser Ser Trp Asp Trp Leu Asp Ile Ser Ser
                340                 345                 350

Val Asn Ser Leu Ala Glu Val His Arg Leu Tyr Val Gly Gly Pro Pro
            355                 360                 365

Leu Glu Lys Glu Pro Arg Glu Leu Phe Val Lys Gly Thr Met Lys Asp
        370                 375                 380

Ile Arg Glu Asn Phe Gln Asp Leu Met Gln Tyr Cys Ala Gln Asp Val
385                 390                 395                 400

Trp Ala Thr His Glu Val Phe Gln Gln Gln Leu Pro Leu Phe Leu Glu
                    405                 410                 415

Arg Cys Pro His Pro Val Thr Leu Ala Gly Met Leu Glu Met Gly Val
                420                 425                 430

Ser Tyr Leu Pro Val Asn Gln Asn Trp Glu Arg Tyr Leu Ala Glu Ala
            435                 440                 445

Gln Gly Thr Tyr Glu Glu Leu Gln Arg Glu Met Lys Lys Ser Leu Met
        450                 455                 460

Asp Leu Ala Asn Asp Ala Cys Gln Leu Leu Ser Gly Glu Arg Tyr Lys
465                 470                 475                 480

Glu Asp Pro Trp Leu Trp Asp Leu Glu Trp Asp Leu Gln Glu Phe Lys
                    485                 490                 495

Gln Lys Lys Ala Lys Lys Val Lys Lys Glu Pro Ala Thr Ala Ser Lys
                500                 505                 510

Leu Pro Ile Glu Gly Ala Gly Ala Pro Gly Asp Pro Met Asp Gln Glu
            515                 520                 525

Asp Leu Gly Pro Cys Ser Glu Glu Glu Glu Phe Gln Gln Asp Val Met
```

```
              530                 535                 540
Ala Arg Ala Cys Leu Gln Lys Leu Lys Gly Thr Thr Glu Leu Leu Pro
545                 550                 555                 560

Lys Arg Pro Gln His Leu Pro Gly His Pro Gly Trp Tyr Arg Lys Leu
                565                 570                 575

Cys Pro Arg Leu Asp Asp Pro Ala Trp Thr Pro Gly Pro Ser Leu Leu
                580                 585                 590

Ser Leu Gln Met Arg Val Thr Pro Lys Leu Met Ala Leu Thr Trp Asp
                595                 600                 605

Gly Phe Pro Leu His Tyr Ser Glu Arg His Gly Trp Gly Tyr Leu Val
            610                 615                 620

Pro Gly Arg Arg Asp Asn Leu Ala Lys Leu Pro Thr Gly Thr Thr Leu
625                 630                 635                 640

Glu Ser Ala Gly Val Val Cys Pro Tyr Arg Ala Ile Glu Ser Leu Tyr
                645                 650                 655

Arg Lys His Cys Leu Glu Gln Gly Lys Gln Leu Met Pro Gln Glu
                660                 665                 670

Ala Gly Leu Ala Glu Glu Phe Leu Leu Thr Asp Asn Ser Ala Ile Trp
            675                 680                 685

Gln Thr Val Glu Glu Leu Asp Tyr Leu Glu Val Glu Ala Glu Ala Lys
            690                 695                 700

Met Glu Asn Leu Arg Ala Ala Val Pro Gly Gln Pro Leu Ala Leu Thr
705                 710                 715                 720

Ala Arg Gly Gly Pro Lys Asp Thr Gln Pro Ser Tyr His His Gly Asn
                725                 730                 735

Gly Pro Tyr Asn Asp Val Asp Ile Pro Gly Cys Trp Phe Phe Lys Leu
                740                 745                 750

Pro His Lys Asp Gly Asn Ser Cys Asn Val Gly Ser Pro Phe Ala Lys
                755                 760                 765

Asp Phe Leu Pro Lys Met Glu Asp Gly Thr Leu Gln Ala Gly Pro Gly
                770                 775                 780

Gly Ala Ser Gly Pro Arg Ala Leu Glu Ile Asn Lys Met Ile Ser Phe
785                 790                 795                 800

Trp Arg Asn Ala His Lys Arg Ile Ser Ser Gln Met Val Val Trp Leu
                805                 810                 815

Pro Arg Ser Ala Leu Pro Arg Ala Val Ile Arg His Pro Asp Tyr Asp
                820                 825                 830

Glu Glu Gly Leu Tyr Gly Ala Ile Leu Pro Gln Val Val Thr Ala Gly
                835                 840                 845

Thr Ile Thr Arg Arg Ala Val Glu Pro Thr Trp Leu Thr Ala Ser Asn
850                 855                 860

Ala Arg Pro Asp Arg Val Gly Ser Glu Leu Lys Ala Met Val Gln Ala
865                 870                 875                 880

Pro Pro Gly Tyr Thr Leu Val Gly Ala Asp Val Asp Ser Gln Glu Leu
                885                 890                 895

Trp Ile Ala Ala Val Leu Gly Asp Ala His Phe Ala Gly Met His Gly
                900                 905                 910

Cys Thr Ala Phe Gly Trp Met Thr Leu Gln Gly Arg Lys Ser Arg Gly
                915                 920                 925

Thr Asp Leu His Ser Lys Thr Ala Thr Thr Val Gly Ile Ser Arg Glu
                930                 935                 940

His Ala Lys Ile Phe Asn Tyr Gly Arg Ile Tyr Gly Ala Gly Gln Pro
945                 950                 955                 960
```

Phe Ala Glu Arg Leu Leu Met Gln Phe Asn His Arg Leu Thr Gln Gln
            965                 970                 975

Glu Ala Ala Glu Lys Ala Gln Gln Met Tyr Ala Ala Thr Lys Gly Leu
            980                 985                 990

Arg Trp Tyr Arg Leu Ser Asp Glu Gly Glu Trp Leu Val Arg Glu Leu
            995                 1000                1005

Asn Leu Pro Val Asp Arg Thr Glu Gly Gly Trp Ile Ser Leu Gln
        1010                1015                1020

Asp Leu Arg Lys Val Gln Arg Glu Thr Ala Arg Lys Ser Gln Trp
        1025                1030                1035

Lys Lys Trp Glu Val Val Ala Glu Arg Ala Trp Lys Gly Gly Thr
        1040                1045                1050

Glu Ser Glu Met Phe Asn Lys Leu Glu Ser Ile Ala Thr Ser Asp
        1055                1060                1065

Ile Pro Arg Thr Pro Val Leu Gly Cys Cys Ile Ser Arg Ala Leu
        1070                1075                1080

Glu Pro Ser Ala Val Gln Glu Glu Phe Met Thr Ser Arg Val Asn
        1085                1090                1095

Trp Val Val Gln Ser Ser Ala Val Asp Tyr Leu His Leu Met Leu
        1100                1105                1110

Val Ala Met Lys Trp Leu Phe Glu Glu Phe Ala Ile Asp Gly Arg
        1115                1120                1125

Phe Cys Ile Ser Ile His Asp Glu Val Arg Tyr Leu Val Arg Glu
        1130                1135                1140

Glu Asp Arg Tyr Arg Ala Ala Leu Ala Leu Gln Ile Thr Asn Leu
        1145                1150                1155

Leu Thr Arg Cys Met Phe Ala Tyr Lys Leu Gly Leu Asn Asp Leu
        1160                1165                1170

Pro Gln Ser Val Ala Phe Phe Ser Ala Val Asp Ile Asp Arg Cys
        1175                1180                1185

Leu Arg
        1190

<210> SEQ ID NO 2
<211> LENGTH: 19
<212> TYPE: DNA
<213> ORGANISM: Artificial Sequence
<220> FEATURE:
<223> OTHER INFORMATION: PRIMER

<400> SEQUENCE: 2
gtccacacca ccaagcagt                                                    19

<210> SEQ ID NO 3
<211> LENGTH: 20
<212> TYPE: DNA
<213> ORGANISM: Artificial Sequence
<220> FEATURE:
<223> OTHER INFORMATION: PRIMER

<400> SEQUENCE: 3
ggtcccaagc actatgctcc                                                   20

<210> SEQ ID NO 4
<211> LENGTH: 20
<212> TYPE: DNA
<213> ORGANISM: Artificial Sequence
<220> FEATURE:

```
<223> OTHER INFORMATION: PRIMER

<400> SEQUENCE: 4
ccttgctgaa tgcaggtgct                                               20

<210> SEQ ID NO 5
<211> LENGTH: 22
<212> TYPE: DNA
<213> ORGANISM: Artificial Sequence
<220> FEATURE:
<223> OTHER INFORMATION: PRIMER

<400> SEQUENCE: 5
tgtgcctgaa atcacactct gt                                            22

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
atggtctgct gagtggttgt                                               20

<210> SEQ ID NO 7
<211> LENGTH: 21
<212> TYPE: DNA
<213> ORGANISM: Artificial Sequence
<220> FEATURE:
<223> OTHER INFORMATION: PRIMER

<400> SEQUENCE: 7
ccctcagagc ccagtttcta c                                             21

<210> SEQ ID NO 8
<211> LENGTH: 20
<212> TYPE: DNA
<213> ORGANISM: Artificial Sequence
<220> FEATURE:
<223> OTHER INFORMATION: PRIMER

<400> SEQUENCE: 8
cccagtttat gaccagccgt                                               20

<210> SEQ ID NO 9
<211> LENGTH: 20
<212> TYPE: DNA
<213> ORGANISM: Artificial Sequence
<220> FEATURE:
<223> OTHER INFORMATION: PRIMER

<400> SEQUENCE: 9
caaggaacgc tcacccaaag                                               20

<210> SEQ ID NO 10
<211> LENGTH: 20
<212> TYPE: DNA
<213> ORGANISM: Artificial Sequence
<220> FEATURE:
<223> OTHER INFORMATION: PRIMER

<400> SEQUENCE: 10
aggggaagcc ctgctctaag                                               20
```

```
<210> SEQ ID NO 11
<211> LENGTH: 21
<212> TYPE: DNA
<213> ORGANISM: Artificial Sequence
<220> FEATURE:
<223> OTHER INFORMATION: PRIMER

<400> SEQUENCE: 11
acaaatgtgt tgtgctcacc c                                             21

<210> SEQ ID NO 12
<211> LENGTH: 35
<212> TYPE: DNA
<213> ORGANISM: Artificial Sequence
<220> FEATURE:
<223> OTHER INFORMATION: PRIMER

<400> SEQUENCE: 12
accgcccgtc accctcctca agtatacttc aaagg                              35

<210> SEQ ID NO 13
<211> LENGTH: 35
<212> TYPE: DNA
<213> ORGANISM: Artificial Sequence
<220> FEATURE:
<223> OTHER INFORMATION: PRIMER

<400> SEQUENCE: 13
accgccaggt cctttgagtt ttaagctgtg gctcg                              35
```